US005756758A

United States Patent [19]
Frank et al.

[11] Patent Number: 5,756,758
[45] Date of Patent: May 26, 1998

[54] PEPTIDE INTERMEDIATES

[75] Inventors: Ronald Frank; Stefan Hoffmann, both of Braunschweig, Germany

[73] Assignee: Gesellschaft fur Biotechnologische Forschung mbH IGBF), Braunschweig, Germany

[21] Appl. No.: 557,032

[22] PCT Filed: Jun. 10, 1994

[86] PCT No.: PCT/EP94/01896

§ 371 Date: Dec. 7, 1995

§ 102(e) Date: Dec. 7, 1995

[87] PCT Pub. No.: WO94/29278

PCT Pub. Date: Dec. 22, 1994

[30] Foreign Application Priority Data

Jun. 11, 1993 [DE] Germany ............................ 43 19 475.3
Jun. 18, 1993 [DE] Germany ............................ 43 20 260.8

[51] Int. Cl.$^6$ ............................ C07D 233/54; C07K 1/06
[52] U.S. Cl. .................................. 548/334.1; 548/338.1; 548/341.5
[58] Field of Search ..................... 548/338.1, 341.5, 548/334.1

[56] References Cited

U.S. PATENT DOCUMENTS

| | | | |
|---|---|---|---|
| 4,866,060 | 9/1989 | Mrozik et al. | 514/250 |
| 4,873,247 | 10/1989 | Goegelman et al. | 514/257 |
| 4,923,867 | 5/1990 | Blizzard et al. | 514/250 |
| 4,978,656 | 12/1990 | Blizzard et al. | 514/63 |
| 5,036,048 | 7/1991 | Watkins | 514/16 |
| 5,256,645 | 10/1993 | Branca et al. | 514/18 |

FOREIGN PATENT DOCUMENTS

| | | | |
|---|---|---|---|
| 0061933 | 10/1982 | European Pat. Off. | 514/16 |
| 0252727 | 1/1988 | European Pat. Off. | 548/338.1 |
| 0 301 742 | 7/1988 | European Pat. Off. | A61K 31/55 |
| 0300189 | 1/1989 | European Pat. Off. | 548/338.1 |
| 0322348 | 6/1989 | European Pat. Off. | 541/18 |
| 0 354 615 | 8/1989 | European Pat. Off. | C07D 491/22 |
| 0 390 532 | 3/1990 | European Pat. Off. | C07D 491/22 |
| 0509354 | 10/1992 | European Pat. Off. | 548/338.1 |
| 1472013 | 1/1967 | France | 548/338.1 |
| WO 91/09961 | 7/1991 | WIPO | C12P 17/18 |
| WO 92/22555 | 12/1992 | WIPO | A01N 43/90 |
| WO 93/10120 | 5/1993 | WIPO | C07D 491/22 |
| 94-01409 | 6/1993 | WIPO | 548/338.1 |

OTHER PUBLICATIONS

Breipohl et al, Tetrahedron Letters, vol. 28, No. 46, pp. 5651–5654 (1987).
Guibe et al, Tetrahedron Letters, vol. 30, No. 20, pp. 2641–2644 (1989).

Blanchflower, Simon E.; Banks, Rhona M.; Everett, Jeremy R.; Manager, Brian R.; Reading, Christopher; New Paraherquanmide Antibiotics With Anthelmintic Activity, The Journal of Antibiotics, May 1991, pp. 492–497.

Conder, G.A.; Jen, L.-W.; Marbury, K.S.; Johnson, S.S.; Gulmond, P.M.; Thomas, E.M.; Lee, B.L.; A Novel Anthelmintic Model Utilizing Jirds, *Meriones unguiculatus*, Infected With *Haemonchus contortus*, J. Parasitol., 76(2), 1990, pp. 168–170.

Conder, G.A.; Johnson, S.S.; Gulmond, P.M.; Cox, D.L.; Lee, B.L.;Concurrent Infections With The Ruminant Nematodes Haemonchus Contortus And Trichostrongylus Colubriformis In Jirds *Meriones unguiculatus*, And Use Of This Model For Anthelmintic Studies, J. Parasitol. 77(4), 1991, pp. 621–623.

Dietz, Alma and Mathews, John, Scanning Electron Microscopy of Selected Members of the *Streptomyces hygroscopicus* Group, Applied Microbiology, Oct. 1969, vol. 18, No. 4, pp. 694–696.

Onions, A.H.S., et al, Smith'Introduction to Industrial Mycology, John Wiley and Sons, New York, pp. 301–302 (1979).

Polonsky, Judith; Merrien, Marie–Annick; Prange, Thierry; Pascard, Claudine; Isolation and Structure (X–Ray Analysis) of Marcfortine A, a New Alkaloid from *Penicillium roqueforti*, J. C. S. Chem. Comm., 1980, pp. 601–602.

Prange, Thierry; Billion, Marie–Annick; Vuilhorgne, Marc; Pascaard, Claudine; Polosky, Judith; Structures of Marcfortine B and C (X–Ray Analysis), Alkaloids From *Penicillium roqueforti*, Tetrahedron Letters, vol. 22, No. 21, pp. 1977–1980, 1981.

Yamazaki, Mikio; Okuyama, Emi; The Structure of Paraherquamide, A Toxic Metabolite From *Penicillum paraherquei*, Tetrahedron Letters, vol. 22, pp. 135–136, 1981.

*Primary Examiner*—Floyd D. Higel
*Attorney, Agent, or Firm*—Kane, Dalsimer, Sullivan, Kurucz, Levy, Eisele and Richard

[57] ABSTRACT

The invention relates to compounds which can be reacted with a carboxyl function with formation of an ester bond, whereby a protective group and, in particular, an anchor group for the carboxyl function is provided. The invention further relates to esters of acids which are obtainable by esterification with a compound according to the invention, and to the use of the compounds according to the invention in peptide synthesis.

8 Claims, 1 Drawing Sheet

PEPTIDE INTERMEDIATES

BACKGROUND OF THE INVENTION

1. Field of the Invention

The invention relates to intermediate compounds useful in peptide synthesis.

2. Brief Description of Related Art

The regioselective chemical reaction of a compound with several reactive chemical functions which are also different requires the protection of all these functions except for that (those) with which a chemical reaction is to be entered into. To protect these functions, molecule groups (protective groups) are introduced. These can subsequently be removed mildly and selectively with reformation of the original function. For complex and multi-stage syntheses, in particular of natural substances, such as oligopeptides and oligonucleotides, various types of protective groups are necessary. They are distinguished by highly different cleavage conditions. A system of protective groups in which the individual types are selectively cleavable in such a way that in each case all other protective groups remain untouched is called orthogonal. The person skilled in the art is familiar with the principle of protective group chemistry. Reference may be made to the literature mentioned in the following text. If the protective group type additionally contains a further reactive function such that it can be linked covalently and stably with a support material for solid-phase synthesis, the person skilled in the art speaks of an "anchor group" or "linker group". A special type of protective group is present if the protective group first has to be brought into a labile form by a chemical reaction inserted before the removal, which can then be removed in a second step under mild conditions. In this case a protected protective group or "safety-catch group" is spoken of. Although two reaction steps are necessary for removal here, a group of this type can offer great advantages:

- it can be very stable against many, even very drastic, reaction conditions, but can be removed by the sequence of two specific, very mild reaction steps;
- the labile intermediates of the protective group can be stable enough that it offers good or better possibilities for the isolation and purification of the final product.

SUMMARY OF THE INVENTION

The object of the present invention is to provide a compound with which a carboxyl function (COOH) can be reacted with formation of an ester bond, by means of which a protective group and, in particular, an anchor group for the carboxyl function can be provided which has the following features:

- the protective or anchor group, for its part, should be protected and be able to be converted into a labile intermediate;
- the labile intermediate should be stable under prespecified reaction conditions, for example those of a solid-phase synthesis of peptides, and allow purification of the intermediates;
- the labile intermediate should decompose in aqueous physiological buffer solution, preferably at neutral pH (approximately pH 7) or almost neutral pH (5 to 9), and be able to reform the original carboxyl function so that the synthesis product having a free carboxyl function is employable directly (without further purification) in a cytobiological or biochemical test experiment.

In particular, this protective group type should be employable as an anchor group for the solid-phase synthesis of peptides, in particular according to the Fmoc/tBu method; compare, for example, Fields & Noble in Int. J. Peptide Protein Res., 35 (1990) 161–214.

According to the invention, for this a compound of the formula

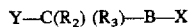

is provided where the compound can be reacted with a carboxyl function by substituting the Y group with formation of an ester bond, by means of which a protective group and, in particular, an anchor group for the carboxyl function is provided, where Y=HO, Cl, Br or I, B=a basic group which is protected by X, only enters into hydrolysis-sensitive acyl compounds and in deprotected form can catalyze the hydrolysis of the ester bond intramolecularly, X=a protective group for the basic group B and blocks its power of catalysis, $R_2$ and $R_3$=any desired radicals which do not adversely affect the formation of the ester bond and its hydrolysis.

BRIEF DESCRIPTION OF THE DRAWINGS

The FIGURE shows graphically the kinetics of peptide removal from some anchor groups in solutions. In graph A (o) represents Compound (9a) in 0.01M $KH_2PO_4/Na_2HPO_4$ (pH 7.5), (Δ) Compound (9a) in 0.01M $KH_2PO_4/Na_2HPO_4$ (pH 7.5), (◇) Compound (9a) in 0.01M TEAAc (pH 7.3), (■) Compound (11a) in 0.01M $KH_2PO_4/Na_2HPO_4$ (pH 7.5) at 50° C. In graph B (●) represents Compound (9a), (○) Compound (8a) and (■) Compound (11a) in 0.01M $KH_2PO_4/Na_2HPO_4$ (pH 7.5) at 25° C.

DETAILED DESCRIPTION OF THE PREFERRED EMBODIMENTS OF THE INVENTION

Figure 1A:
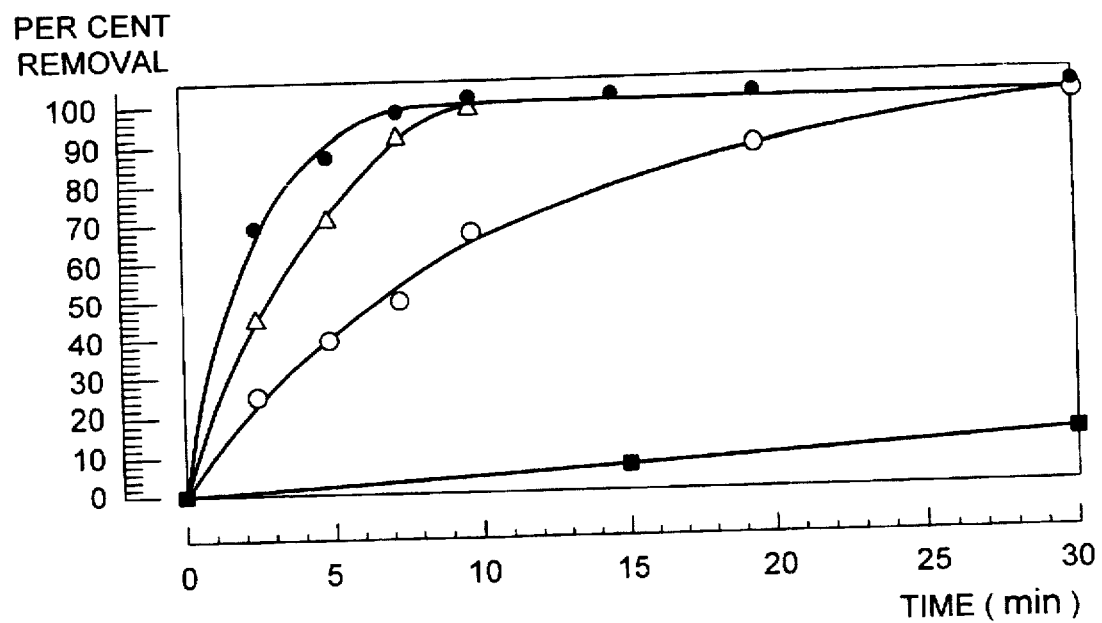
Figure 1B:
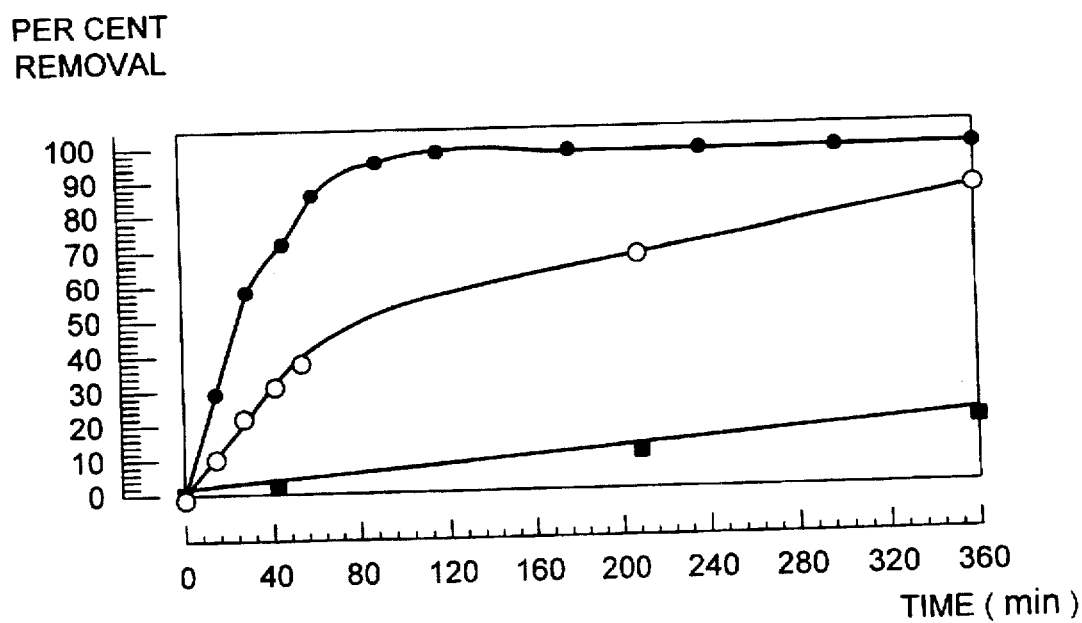

As already said, the person skilled in the art is familiar with the principle of protective group chemistry. For explanation, reference may be made to the following prior art. Protective group: for example Green & Wuts, Eds., Protective Groups in Organic Synthesis, 2nd Ed., 1991, John Wiley & Sons, NY. Anchor group or linker group: for example Breipohl et al. in Tetrahedron Lett., 28 (1987) 5651–5654; Guibe et al., in Tetrahedron Lett., 30 (1989) 2641–2644. Protected protective group (safety-catch group): Patek in Int. J. Peptide Protein Res., 42 (1993) 97–117. Electron-withdrawing protective group for a basic group, where the first reduces the basicity of the basic group: Gross & Meienhofer, Eds., The Peptides, Vol. 3, 1981, Academic Press, NY.; Patek in Int. J. Peptide Protein Res., 42 (1993) 97–117, in particular 112.

The chemical bond between protective group and carboxyl function should thus be an ester bond. This ester bond can be introduced by reaction of the carboxyl function with a hydroxyl function or a halogen function of the compound according to the invention. Carboxylic acid esters can be cleaved more or less easily in aqueous solution by base catalysis. The protective group therefore has a basic function B which can catalyse the hydrolysis of the ester bond intramolecularly. This basic function B must not enter into hydrolysis-stable acyl compounds itself, as otherwise the carboxyl compound to be protected could be transferred to B and thus no hydrolytic cleavage would occur. This basic function is moreover protected by a group X, which reduces the basicity of the group B to the extent that an intramolecularly catalysed hydrolysis of the ester compound can only take place after removal of the group X. The group X is stable under the conditions of a synthesis starting at $R_1$.

The following reaction scheme is intended to illustrate the utility of the compound according to the invention in greater detail. In this scheme:

$R_1$=radical of the compound to be protected, $R_2$ and $R_3$=radicals of the protective group which do not participate in its function (if $R_2$ or $R_3$ contain an additional reactive function for linkage with support materials, for example —COOH, —OH, —NH$_2$ or —SH, then the protective group is employed as an anchor group), B=a basic function and X=protective group of the basic function.

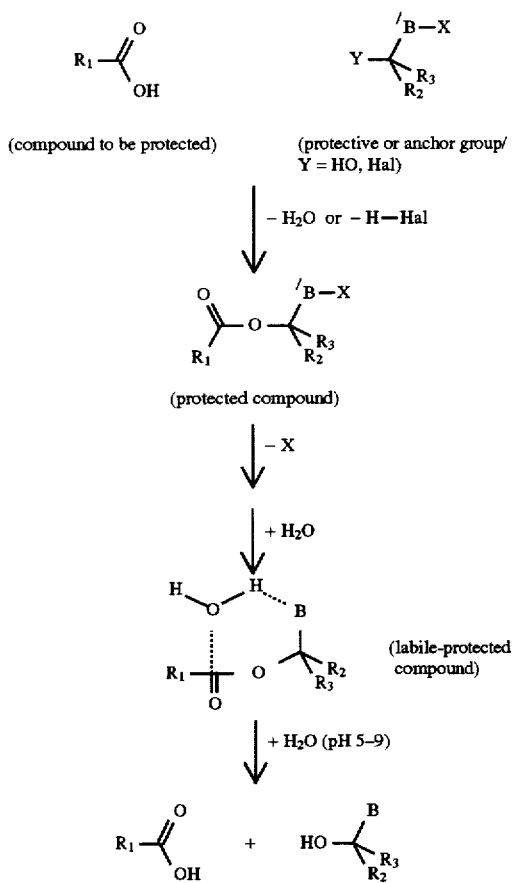

According to the invention, B can be an aromatic nitrogen-containing five-membered ring and/or X can be an electron-withdrawing protective group which greatly reduces the basicity of the basic group B, and/or $R_2$=H, alkyl or aryl, in each case without a reactive function, and/or $R_3$=H, alkyl or aryl, in each case without a reactive function; HOOC, whereby an anchor group can be provided; or alkyl or aryl, in each case substituted by a reactive function which can be HO, H$_2$N, HS or HOOC, whereby an anchor group can be provided.

For example, B can [lacuna] imidazolyl or imidazolylmethylene which is methyl-substituted in the ring. X a urethane or alkoxycarbonyl protective group.

$R_2$=$C_{1-12}$-alkyl or phenyl and/or $R_3$=$C_{1-12}$-alkyl, phenyl, HOOC-$C_{1-12}$-alkyl, HOOC-phenyl, HO-$C_{1-12}$-alkyl, HO-phenyl, H$_2$N—$C_{1-12}$-alkyl, H$_2$N-phenyl, HS-$C_{1-12}$-alkyl or HS-phenyl.

Preferably, B is imidazol-4-ylmethylene, imidazol-4-yl, imidazol-2-yl or 5-methylimidazol-4-yl and/or X is tert-butoxycarbonyl (Boc).

According to a further embodiment, the invention relates to esters of acids, which are obtainable by esterification with a compound according to the invention. Acids of this type can be mono-, di- or oligopeptides and their derivatives.

According to a further embodiment, the invention finally relates to the use of compounds and esters according to the invention in peptide synthesis.

Experimental section

General experimental section

The following analytical spectroscopy apparatuses were used.- $^1$H-NMR/$^{13}$C-NMR: Bruker Model AM-300 and WM-400 using tetramethylsilane (TMS) as internal standard.- Signal multiplicity: s=singlet, d=doublet, t=triplet, q=quartet, $^nJ_{H,H}$=magnetic coupling over n bonds between adjacent protons.-

FAB-MS: Kratos MS 50 TC RF with neutral xenon beam (8–9 kV) and Finnigan Mat. Mass SW spectrometer 8430 using 3-nitrobenzyl alcohol as matrix. The samples were introduced in DMSO. TV/VIS: Carl Zeiss Model PMQ II in quartz cuvettes having an optical length of 10 mm. $\epsilon$(dibenzofulvene-piperidine adduct/MeOH)—5570. RP-C$_{18}$ HPLC: analyt. HPLC: Pharmacia/LKB Pump P 3500, liquid chromatography controller LCC 500 Plus or LKB 2249 gradient pump, LKB 2141 variable wavelength monitor, three-channel flat bed recorder on Machery-Nagel Nucleosil 300-7 C$_{18}$ 250×4.

Special experimental section 2-(1H-5-methylimidazol-4-yl)-2-hydroxyacetic acid (1)

(C$_6$H$_8$N$_2$O$_3$) 18.25 g (0.17 mol) of 4-methyl-5-1H-imidazolcarbaldehyde [prepared according to the literature procedure: Papadopoulos, E. P., Jarrar, A. and Issidorides, C. H., J. Chem. Soc. Chem. Comm. 615 (1966)] are dissolved in 80 ml of water and 23.65 g (0.36 mol) of potassium cyanide, 30 ml of conc. hydrochloric acid (37%) and 66 ml of acetic anhydride are added at 0° C. with stirring. The mixture is stirred at 0° C. for 1 h and at RT for a further 24 h. 15 ml of conc. hydrochloric acid and 66 ml of acetic anhydride are added at RT and the mixture is stirred at RT for a further 24 h. After adding 250 ml of water and 250 ml of conc. hydrochloric acid, the mixture is heated to 100° C. under reflux. After 2 h, a further 250 ml of conc. hydrochloric acid are added and the mixture is stirred at 80° C. for 12 h. The solution is concentrated and purified either by prep. HPLC chromatography on Latek RP-C$_{18}$ HL 10μ 300×40 (yield 95% of theory) or (1) via the silver salt according to Stewart, C. P., J. Med. Chem. 130 (1923). The residue is dissolved in water and precipitated in nitric acid solution using silver nitrate. After filtration of the solution, barium hydroxide is added and the silver salt of (1) is filtered off together with excess silver oxide. The filtrate is suspended in water and hydrogen sulphide is passed in. After filtration of the solution, excess barium is precipitated by careful addition of sulphuric acid. After repeated filtration, the solution is concentrated and (1) is obtained by repeated fractional crystallization from aqueous ethanol.- Yield 42% of theory.

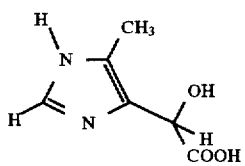

R₂: H
R₃: COOH
B: 5-methylimidazol-4-yl
X: H

¹H-NMR (400 MHz, D₂O ): δ=8.57 (s, 1H, 2-H), 5.59 (s, 1H, C$\underline{H}$OH), 2.33 (s, 3H, CH₃).

¹³C-NMR (75 MHz, D₂O ): δ=174.0 (s, COOH), 135.2 (d, C-2), 132.3 (s, C-5), 119.9 (d, C-4), 65.5 (d, $\underline{C}$HOH), 9.5 (q, CH₃).- MS (FAB): M/Z (3-NBA)=157 ([M+H].).

2-(1H-Imidazol-4-yl)-2-hydroxyacetic acid (2)

(C₅H₆N₂O₃) The synthesis was carried out analogously to (1) starting from 4-1H-imidazolecarbaldehyde. [Prepared according to the literature procedure: Weidenhagen, R. and Herrmann, R., Chem. Ber. 1955 (1953)] Yield 92% of theory (after RP-C₁₈ chromatography (eluent: water/0.1% TFA). Or it is fractionally crystallized as under (1) from water/ethanol.

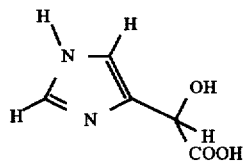

R₂: H
R₃: COOH
B: Imidasol-4-yl-
X: H

¹H-NMR (400 MHz, D₂O ): δ=8.70 (s, 1H, 2-H), 7.51 (s, 1H,4-H), 5.54 (s, 1H, C$\underline{H}$OH).

¹³C-NMR (75 MHz, D₂O ): δ=173.5 (s, COOH), 135.0 (d, C-2), 131.2 (s, C-5), 117.9 (d, C-4), 65.2 (d, $\underline{C}$HOH).- MS (FAB): M/Z (3-NBA)=143 ([M+H].).

2-(1H-Imidazol-2-yl)-2-hydroxyacetic acid (3)

(C₅H₆N₂O₃) The synthesis was carried out analogously to (1) starting from 2-1H-imidazolcarbaldehyde [commercially available, e.g. Aldrich]. Yield 82% of theory (RP-C18-chromatography/eluent water/0.1% TFA).

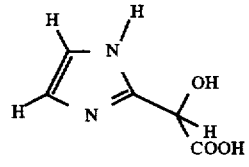

R₂: H
R₃: COOH
B: Imidazol-2-yl-
X: H

¹H-NMR (400 MHz, D₂O): δ=7.38 (s, 2H, H-1), 5.69 (1H, s, H-2).- ¹³C-NMR (75 MHz, D₂O): δ=171.1 (s, COOH), 144.0 (s, C-2), 120.1 (d, C-5/C-5), 66.2 (d, $\underline{C}$HOH).- MS (FAB): M/Z (3-NBA)=143 ([M+H].).

3-(N$^{im}$-tert-butoxycarbonylimidazol-4-yl)-2-hydroxypropionic acid (4)

(C₁₁H₁₆N₂O₅) 248 mg of 3-1H-imidazol-2-hydroxypropionic acid (1.6 mmol) [commercially available, e.g. Sigma] are suspended with stirring at 4° C. with addition of 223 μl (1.6 mmol) triethylamine [note: added after date of Application] in 2.5 ml of abs. DMF and 344 μl (2.4 mmol) of tert-butoxycarbonyl azide are added. The mixture is stirred at 4° C. for 2 d and the solution is completely evaporated at 40° C. on a rotary evaporator. The residue is dissolved in abs. dioxane and the resulting crystalline precipitate is filtered off. Lyophilization of the filtrate in a high vacuum yields a colourless, viscous syrup. 356 mg (1.4 mmol), yield 87% of theory.

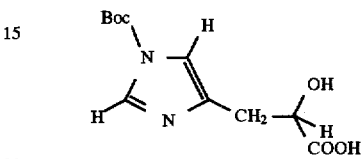

R₂: H
R₃: COOH
B: Imidazol-4-ylmethyl
X: tert-Butoxycarbonyl-(Boc)

¹H-NMR (300 MHz, CDCl₃): δ=8.15 (d, 1H, 2-H, $^4J_{H,H}$=1.25 Hz), 7.27 (s, 1H, 4-H), 4.39 (t, 1H, C$\underline{H}$OH, $^3J_{H,H}$=4.5 Hz), 3.14 (AB-dd, 1H, —CH₂—, $^2J_{H,H}$=14.8 Hz, $^3J_{H,H}$=4.0 Hz), 3.02 (AB-dd, 1H, —CH₂—, $^2J_{H,H}$=14.8 Hz, $^3J_{H,H}$=5.0 Hz), 1.57 (s, 9H, CH₃).- ¹³C-NMR (75 MHz, CDCl₃): δ=176.1 (s, COOH), 146.3 (s, N—COO—), 136.8 (d, C-2), 135.9 (s, C-5), 116.1 (d, C-4), 86.4 (s, $\underline{C}$(CH₃)₃), 68.5 (d, CHOH), 67.0 (t, —CH₂—), 27.8 (q, CH₃).- MS (FAB, DCHA-derivative): M/Z (3-NBA)=295 ([M+K].), 279 ([M+Na].), 257 ([M+H].), 201 ([M-57]., -tBu), 182 ([DCHA+H].).

2-(N$^{im}$-tert-butoxycarbonylimidazol-4-yl)-2-hydroxyacetic acid (5)

(C₁₀H₁₄N₂O₅) Synthesis was carried out analogously to (4) starting from (2). Yield 52% of theory.

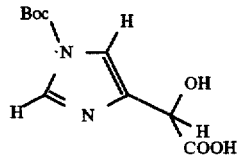

R₂: H
R₃: COOH
B: Imidazol-4-ylmethyl
X: tert-Butoxycarbonyl-(Boc)

¹H-NMR (400 MHz, CDCl₃): δ=8.15 (s, 1H, 2-H), 7.27 (s, 1H, 4-H), 5.14 (s, 1H, C$\underline{H}$OH), 1.58 (s, 9H, CH₃).-¹³C-NMR (75 MHz, CDCl₃: δ=176.1 (s, COOH), 146.3 (s, N—COO—), 136.8 (d, C-2), 135.9 (s, C-5), 116.1 (d, C-4), 86.4 (s, $\underline{C}$(CH₃)₃), 66.5 (d, CHOH), 27.8 (q, CH₃).

2-(N$^{im}$-tert-Butoxycarbonyl-5-methylimidazol-4-yl)-2-hydroxyacetic acid (6)

(C₁₁H₁₆N₂O₅) Synthesis was carried out analogously to (4) starting from (1) by reaction with di-tert-butyl pyrocarbonate or tert-butoxycarbonyl azide in DMF. Yield 273 mg (1.1 mmol) 67% of theory (white lyophilizate from dioxane).

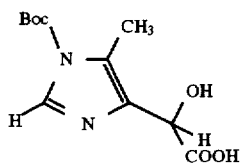

R$_2$: H
R$_3$: COOH
B: 5-methylimidazol-4-yl
X: tert-Butoxycarbonyl- (Boc)

$^1$H-NMR (400 MHz, CDCl$_3$): δ=8.15 (s, 1H, 2-H), 5.14 (s, 1H, CHOH), 2.46 (s, 3H, CH$_3$), 1.58 (s, 9H, CH$_3$).-$^{13}$C-NMR (75 MHz, CDCl$_3$): δ=174.6 (s, COOH), 147.1 (s, N—COO—), 137.0 (d, C-2), 136.2 (s, C-5), 127.2 (s, C-4), 86.4 (s, C(CH$_3$)$_3$), 66.5 (d, CHOH), 27.8 (q, CH$_3$).-MS(FAB): M/Z (3-NBA)=270 ([M+Na].), 257 ([M+H].), 201 ([M-57+H]., tBu).

2-(N$^{im}$-tert-Butoxycarbonylimidazol-2-yl)-2-hydroxyacetic acid (7)

(C$_{10}$H$_{14}$N$_2$O$_5$) Synthesis was carried out analogously to (4) starting from (3) by reaction with di-tert-butyl pyrocarbonate in DMF. Yield 51% of theory.

$^1$H-NMR (400 MHz, CDCl$_3$): δ=8.62 (s, 1H, 4-H), 7.27 (s, 1H, 5-H), 5.56 (s, 1H, CHOH), 1.58 (s, 9H, CH$_3$).

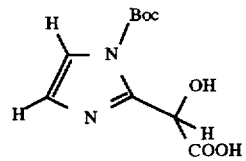

R$_2$: H
R$_3$: COOH
B: Imidazol-2-yl-
X: tert-Butoxycarbonyl- (Boc)

3-(1H-Imidazol-4-yl)-2-(phenylalanylphenylalanylglycyloxy)propionyl-β-alanine (8a)

(C$_{29}$H$_{34}$N$_6$O$_7$)
MS(FAB): M/Z (3-NBA)=712 ([M+Cs+H].), 579 ([M+H].).

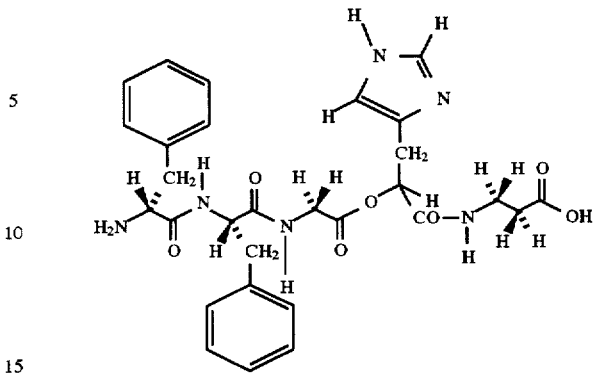

R: H-Phe-Phe-Gly-O-
R$_2$: H
R$_3$: CONH—CH$_2$—CH$_2$—COOH
B: Imidazol-4-ylmethyl-
X: H

[2-(1H-(5-Methylimidazol-4-yl)-2-(phenylalanylphenyl-alanylglycyloxy)]acetyl-β-alanine [sic] (9a)
(C$_{29}$H$_{34}$N$_6$O$_7$)
MS(FAB): M/Z (3-NBA)=712 ([M+Cs+H].), 579 ([M+H].).

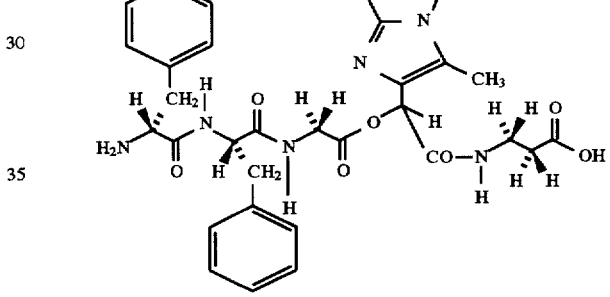

R$_1$: H-Phe-Phe-Gly-O-
R$_2$: H
R$_3$: CONH—CH$_2$—CH$_2$—COOH
B: 5-Methyl-4-1H-imidazolyl-
X: H

[2-1H-Imidazol-4-yl-2-(Phenylalanylphenylalanylglycyloxy)]acetyl-β-alanine carrier (10b)

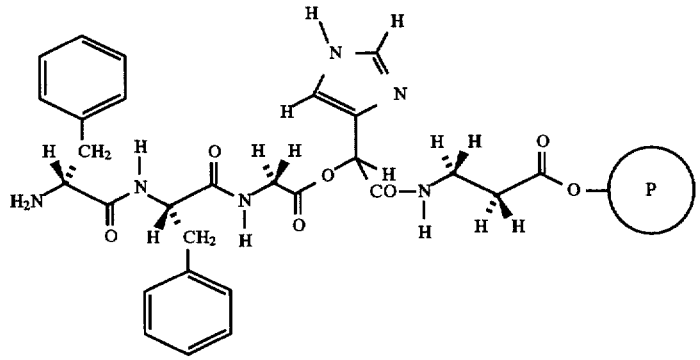

R₁: H-Phe-Phe-Gly-O-
R₂: H
R₃: CONH—CH₂—CH₂—COOH
B: 5-Methylimidazolyl-4-yl-
X: H
[Phenylalanylphenylalanylglycyloxy)]-acetyl-β-alanine
(11a)

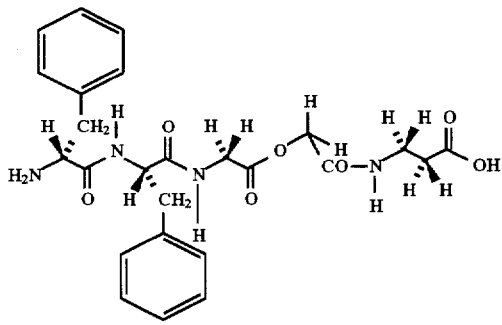

R₁: H-Phe-Phe-Gly-O
R₂: H
R₃: CONH—CH₂—CH₂—COOH
B: H

The protective group concept was investigated as exemplified by the abovementioned compounds where B=1H-imidazolyl and X=tert-butyloxycarbonyl both in solution and bonded to a solid paper support (Whatman 3 MM) with respect to specific use as an orthogonal anchor group for solid-phase peptide synthesis.

Test in solution

The compounds (8) and (9) were synthesized on a p-benzyloxybenzyl-derivatized polystyrene resin ('Wang resin' from Novabiochem). To do this, N^β-9-fluorenylmethoxycarbonyl-β-alanine was esterified on the resin by activation of the carboxyl function with mesitylenesulfonyl-3-nitro-1,2,4-triazole (MSNT) with N-methylimidazole (MeIm) catalysis in DCM [Blankemeyer-Menge, B. and Frank, R., Tetrahedron Lett, 31, 1701 (1990)]. After removal of the amino protective group using an excess of 20% piperidine in DMF, (4) or (6) was coupled to the bound H-βalanine unit by N,N-diisopropylcarbodiimide (DIC) (1.2 eq.)/ hydroxybenzotriazole (HOBt) (2.0 eq.) activation of the carboxyl function in DMF. The stepwise synthesis of the tripeptide H-Phe-Phe-Gly began with the MSNT/MeIm-activated esterification of the N^α-Fmoc-Gly-OH on the anchor group. Subsequently, the procedure was according to customary peptide synthesis conditions with DIC/HOBt activation according to the N^α-Fmoc/tBu strategy [Fields, G. B. and Noble, R. L., Int. J. Peptide Protein Res. 35, 161–214 (1990)]. All coupling steps proceeded with almost quantitative yield (UV/VIS analysis of the dibenzofulvene/piperidine adduct). The compounds (8a) and (9a) were removed from the solid support using trifluoroacetic acid (TFA)/dichloromethane (DCM) (1:1) (2.5% triisobutylsilane (TIBS), 2.5% water) and purified by RP-C₁₈ chromatography. In this process the imidazolyl protective group X=Boc is removed at the same time. As a direct comparison with the anchor groups specifically described here, the compound H-Phe-Phe-Gly-O-glycolic acid-βAla-OH (11a) was synthesized on solid phase according to the process described above, removed as above and purified by RP-C₁₈-HPLC.

The compounds (8a), (9a) deprotected on the imidazolyl radical (B) and now labile-protected and the comparison substance (11a) were studied in solution for the lability of the ester bond to the aqueous buffers mentioned below. Table 1 presents the results.

Buffers used
(a) NaH₂PO₄/Na₂HPO₄/0.1M/pH 7.0/H₂O
(b) NaH₂PO₄/Na₂HPO₄/0.1M/pH 7.5/H₂O
(c) NaH₂PO₄/Na₂HPO₄/0.01M/pH 7.0/H₂O
(d) NaH₂PO₄/Na₂HPO₄/0.01M/pH 7.5/H₂O
(e) Na₃BO₄/H₃BO₄/0.05M/pH 7.6/H₂O
(f) Na₃BO₄/H₃BO₄/0.05M/pH 8.0/H₂O
(g) tris-Hydroxymethylaminomethane hydrochloride (tris HCl)/0.01M/pH 7.6/H₂O
(h) tris-Hydroxymethylaminomethane hydrochloride (tris HCl)/00.1M/pH 8.0/H₂O
(i) NaHCO₃/Na₂CO₃/0.05M/pH 9.6/H₂O
(j) NaHCO₃/Na₂CO₃/0.05M/pH 10.0/H₂O
(k) DMF/water=1:9 (pH 7.0)
(l) Triethylammonium acetate (TEAAc)/0.01M/pH 7.0/H₂O

TABLE 1

Progress of the ester hydrolysis reaction [%] of (8) and (9) in comparison with (11) in various buffers at 25° C. and 50° C.; (—) = not determined, * = 50° C.

| | (c) NaH₂PO₄/Na₂HPO₄/0.01M/ pH 7.0/H₂O (25° C.) | | | | | | (c) NaH₂PO₄/Na₂HPO₄/0.01M/ pH 7.0/H₂O (50° C.) | | | | | |
|---|---|---|---|---|---|---|---|---|---|---|---|---|
| min | 120 | 240 | 510 | 600 | 720 | 840 | 10 | 15 | 30 | 45 | 120 | 270 | 840 |
| (8) | (—) | 33 | 55 | (—) | 100 | 100 | (—) | (—) | (—) | 46 | (—) | 100 | 100 |
| (9) | 45 | (—) | (—) | 100 | 100 | 100 | 100 | 100 | 100 | 100 | 100 | 100 | 100 |
| (11) | (—) | (—) | (—) | (—) | (—) | 5 | (—) | (—) | (—) | (—) | 20 | (—) | (—) |

| | (d) NaH₂PO₄/Na₂HPO₄/0.01M/ pH 7.5/H₂O (25° C.) | | | | | | (c) NaH₂PO₄/Na₂HPO₄/0.01M/ pH 7.5/H₂O (50° C.) | | | | | |
|---|---|---|---|---|---|---|---|---|---|---|---|---|
| min | 45 | 150 | 600 | 720 | 780 | 840 | 5 | 30 | 45 | 60 | 120 | 270 | 510 |
| (8) | (—) | (—) | (—) | (—) | (—) | (—) | (—) | (—) | 46 | (—) | (—) | 100 | 100 |
| (9) | 45 | 66 | 100 | 100 | 100 | 100 | 5 | (—) | (—) | 100 | 100 | 100 | 100 |
| (11) | (—) | (—) | (—) | (—) | (—) | 5 | (—) | 0 | (—) | (—) | 22 | (—) | (—) |

TABLE 1-continued

Progress of the ester hydrolysis reaction [%] of
(8) and (9) in comparison with (11) in various buffers at
25° C. and 50° C.; (—) = not determined, * = 50° C.

| | (j) NaHCO$_3$/Na$_2$CO$_3$/0.05M/ pH 10.0 (25° C.) | | | | | | tris/0.01M/H$_2$O | | |
|---|---|---|---|---|---|---|---|---|---|
| min | 2.5 | 5 | 30 | 45 | 510 | 840 | g/720/50° C. | g/270/25° C. | g/45/25° C. |
| (8) | 100 | 100 | 100 | 100 | 100 | 100 | (—) | 50 | 48 |
| (9) | (—) | 100 | 100 | 100 | 100 | 100 | 100 | (—) | (—) |
| (11) | (—) | (—) | (—) | 49* | (—) | (—) | (—) | (—) | (—) |

Test on the polymeric support

The polymer-bound compounds analogous to (8a), (9a) and (11a) were synthesized as above but on round paper filters (Whatman 3 MM). Treatment with TFA/DCM (2.5% TIBS, 2.5% H$_2$O) in this specific case only removes the imidazolyl protective group X=Boc, but does not touch the ester bond between C-terminal carboxyl function and the solid support (polymer-bound compounds are marked in the following by a b). Additionally to (8b), (9b) and (11b), a compound (10b) was synthesized which was bound to the solid phase by the anchor molecule (5). After removing the protective group X from polymer-bound (8b)-(10b), the filter is washed for 2×5 min using the removal reagents, 3×10 min using 1% HCl in meth anol/water (1:1) and 3×10 min using 1M acetic acid/water and dried in HV for 12 h. No tripeptide H-Phe-Phe-Gly-OH can be detected in the wash solutions.

The compounds (8a), (9a) [sic] deprotected on the imidazolyl radical and now labile-protected and the comparison substance (11a) [sic] were studied in solution for the lability of the ester bond to the aqueous buffers mentioned below. Table 1 [sic] shows the results.

TABLE 2

Removal of the tripeptide H—Phe—Phe—Gly—OH from
the solid phase-bound compounds (8b)–(11b) in various
buffers at 50° C. over 12 h. The errors in measurement are
affected by an error of about 20% [sic].

| | (a) | (b) | (c) | (d) | (e) | (f) | (h) | (k) | (l) |
|---|---|---|---|---|---|---|---|---|---|
| (8b) | 100 | 100 | 100 | 100 | 100 | 100 | 80 | 5 | 90 |
| (9b) | 100 | 100 | 100 | 100 | 100 | 100 | 90 | 5 | 60 |
| (10b) | 100 | 100 | 100 | 100 | 100 | 100 | 50 | 5 | 80 |
| (11b) | nd | 25 | nd | 25 | 20 | 40 | nd | 1 | 25 |

The results show clearly that the protective group protected with X is stable to the synthesis of R$_1$ under the basic reaction conditions (e.g. 20% piperidine in DMF)

that the ester bond of the protective group is stable to the carboxyl compound under acidic aqueous conditions and the correspondingly protected compounds can be purified that the basic function of the protective or anchor group type leads to a drastically increased hydrolysis rate in comparison with the unsubstituted glycolic acid derivatives.

that removal of the protective group (without X) is also possible under neutral reaction conditions (pH=7).

3-(N$^{im}$-tert-butoxycarbonylimidazol-4-yl)-2-bromopropionic acid (12)

(C$_{11}$H$_{15}$BrN$_2$O$_4$) Synthesis was carried out analogously to (4) starting from 3-1H-imidazol-4-yl-2-bromopropionic acid (e.g. commercially available from Sigma). Yield 67% of theory.

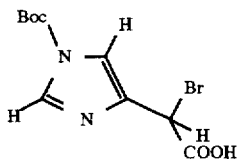

R$_2$: H
R$_3$: COOH
B: Imidazol-4-yl
X: tert-Butoxycarbonyl- (Boc)
and hydroxyl function (—OH) replaced by bromo function (—Br)

$^1$H-NMR (400 MHz, CDCl$_3$): δ=8.15 (s, 1H, 2-H), 7.27 (s, 1H, 4-H), 5.55 (s, 1H, CHBr), 1.58 (s, 9H, CH$_3$).- $^{13}$C-NMR (75 MHz, CDCl$_3$): δ=176.1 (s, COOH), 146.3 (s, N—COO—), 136.8 (d, C-2), 135.9 (s, C-5), 116.1 (d, C-4), 86.4 (s, C(CH$_3$)$_3$), 73.5 (d, CHOH), 27.8 (q, CH$_3$).

Abbreviations used

Amino acid derivatives according to IUPAC-IUB [J. Biol. Chem. 260, 14 (1983)]

Boc tert-butyloxycarbonyl
DCHA dicyclohexylammonium
DCM dichloromethane
DIC N,N'-diisopropylcarbodiimide
DMF dimethylformamide
DMSO dimethyl sulphoxide
FAB-MS "fast atom bombardment" mass spectroscopy
Fmoc 9-fluorenylmethoxycarbonyl
Hal Halogen
HOBt N-hydroxybenzotriazol
HPLC high-pressure liquid chromatography
HV high vacuum
MeIm N-methylimidazole
MSNT mesitylenesulphonyl-3-nitro-1,2,4-triazole
3-NBA 3-nitrobenzyl alcohol
NMR nuclear magnetic resonance spectroscopy
TIBS triisobutylsilane
TFA trifluoroacetic acid

We claim:

1. Oligopeptide esterified with a compound of the formula:

Y—C(R$_2$) (R$_3$)—B—X wherein

Y represents one of hydroxyl, chlorine, bromine or iodine;
B is a 5-membered heterocyclic ring wherein nitrogen is a hetero atom and the ring may be linked to the Y—C(R$_2$)—(R$_3$) moiety by an alkylene bridge;

X is a monovalent electron-withdrawing group which forms together with B a protected protective group;

$R_2$ represents hydrogen, alkyl, alkyl having a non-reactive substituent, aryl or aryl having a non-reactive substituent; and $R_3$ is selected from the group consisting of hydrogen, alkyl, alkyl having a non-reactive substituent, aryl, aryl having a non-reactive substituent, hydroxy-substituted alkyl, hydroxy-substituted aryl, amino-substituted alkyl, amino-substituted aryl, thio-substituted alkyl, thio-substituted aryl, carboxyl-substituted alkyl, carboxyl-substituted aryl and a monovalent carboxyl group.

2. Oligopeptide according to claim 1, wherein B is selected from the group consisting of imidazolyl, imidazolyl methyl-substituted on the ring, imidazolylmethylene and imidozolylmethylene methyl-substituted on the ring.

3. Oligopeptide according to claim 1, wherein X is a group selected from the group consisting of a urethane and an alkoxycarbonyl.

4. Oligopeptide according to claim 1, wherein $R_2$ represents one of $C_1$ to $C_{12}$ alkyl or phenyl.

5. Oligopeptide according to claim 1, wherein $R_3$ represents $C_1$ to $C_{12}$ alkyl, phenyl, HOOC—$C_1$ to HOOC—$C_{12}$ alkyl, HOOC—phenyl, HO—$C_1$ to HO—$C_{12}$ alkyl, HO—phenyl, $H_2N$—$C_1$ to $H_2N$—$C_{12}$ alkyl, $H_2N$—phenyl, HS—$C_1$ to HS—$C_{12}$ alkyl or HS—phenyl.

6. Oligopeptide according to claim 2, wherein B represents imidazol-4-yl-methylene, imidazol-4-yl, imidazol-2-YI or 5-methyl-imidazol-4-yl.

7. Oligopeptide according to claim 3, wherein X represents tertbutoxycarbonyl.

8. Process for the synthesis of an oligopeptide according to claim 1, which comprises;

providing an un-esterfied oligopeptide; and esterfying said oligopeptide with a compound of the formula Y—C($R_2$) ($R_3$)—B—X according to claim 1.

* * * * *